United States Patent [19]

Nedelec et al.

[11] 4,100,278

[45] Jul. 11, 1978

[54] NOVEL BENZAZEPINES

[75] Inventors: Lucien Nedelec, Le Raincy; Daniel Fréchet, Paris; Claude Dumont, Nogent-sur-Marne; Marie-Helene Kannengiesser, Paris, all of France

[73] Assignee: Roussel Uclaf, Paris, France

[21] Appl. No.: 782,747

[22] Filed: Mar. 30, 1977

[30] Foreign Application Priority Data

Mar. 31, 1976 [FR] France ................................ 76 09333

[51] Int. Cl.² .................... A61K 31/55; C07D 223/16
[52] U.S. Cl. ............................... 424/244; 260/239 BB
[58] Field of Search .................. 260/239 BB; 424/244

[56] References Cited

U.S. PATENT DOCUMENTS 3,423,401   1/1969   Morren ........................... 260/239 BC Primary Examiner—Donald G. Daus
Assistant Examiner—D. B. Springer
Attorney, Agent, or Firm—Hammond & Littell

[57] ABSTRACT

Novel benzazepines of the formula

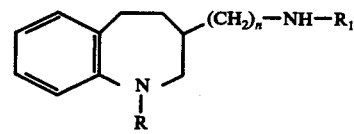

wherein $n$ is 0 or 1 and R and $R_1$ are individually selected from the group consisting of hydrogen and methyl with the proviso that when $R_1$ is methyl, R is also methyl and their non-toxic, pharmaceutically acceptable acid addition salts having antidepressive activity and novel intermediates and processes for the preparation of the said compounds.

11 Claims, No Drawings

NOVEL BENZAZEPINES

STATE OF THE ART

French Pat. No. 1,472,930 describes 2-benzazepines but of a different formula and having an activity on the central nervous system.

OBJECTS OF THE INVENTION

It is an object of the invention to provide the novel benzazepines of formula I and their non-toxic, pharmaceutically acceptable acid addition salts.

It is another object of the invention to provide a novel process for the preparation of a compound of formula I and to novel intermediates.

These and other objects and advantages of the invention will become obvious from the following detailed description.

THE INVENTION

The novel products of the invention are selected from the group consisting of benzazepines of the formula

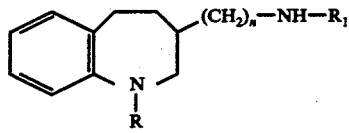

wherein $n$ is 0 or 1 and R and $R_1$ are individually selected from the group consisting of hydrogen and methyl with the proviso that when $R_1$ is methyl, R is also methyl and their non-toxic, pharmaceutically acceptable acid addition salts. The preferred compounds are those where $n$ is 1.

Examples of suitable acids for the preparation of the non-toxic, pharmaceutically acceptable acid addition salts are inorganic acids such as hydrochloric acid, hydrobromic acid, hydroiodic acid, nitric acid, sulfuric acid or phosphoric acid and organic acids such as acetic acid, formic acid, benzoic acid, maleic acid, fumaric acid, succinic acid, tartaric acid, citric acid, oxalic acid, glyoxylic acid or aspartic acid and alkane sulfonic acids such as methane sulfonic acid and aryl sulfonic acids such as benzene sulfonic acid.

The novel process of the invention for the preparation of a compound of formula I wherein $n$ is 1 comprises reacting a compound of the formula

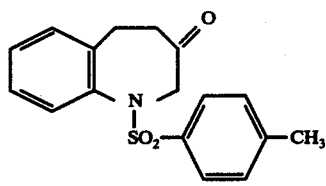

with sodium cyanide to produce a compound of the formula

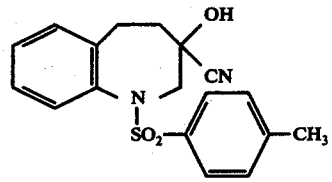

deshydrating the latter to obtain a compound of the formula

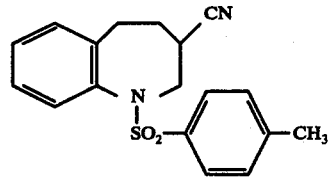

where the dotted line is a double bond in the 2,3 or the 3,4-position of the benzazepine and reducing the latter to form a compound of the formula

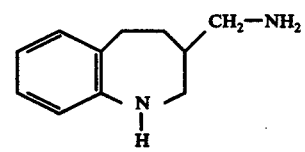

and recovering the latter and if desired salifying the latter or reacting the compound of formula Ia with formic acid to obtain a compound of the formula

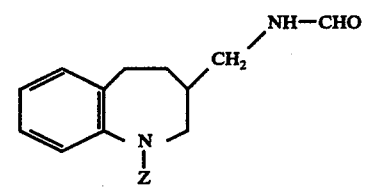

wherein Z is hydrogen or formyl and reducing the latter to form a compound of the formula

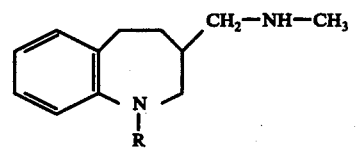

wherein R has the above definition which product may be salified, if desired.

In a preferred mode of the process of the invention, the compound of formula II and sodium cyanide are reacted in the presence of acetic acid in aqueous ethanol and the deshydration of the compound of formula III is effected with heating with thionyl chloride in anhydrous pyridine. The reduction of the compound of formula IV is effected with sodium in ethanol. The reaction of a compound of formula Ia with formic acid is preferably effected with heating in the absence of a solvent and the reduction of the compound of formula V is effected with lithium aluminum hydride in an anhydrous organic solvent such as tetrahydrofuran.

The process of the invention for the preparation of a compound of formula I wherein n is 0 comprises reacting the compound of formula II with hydroxylamine hydrochloride to obtain a compound of the formula

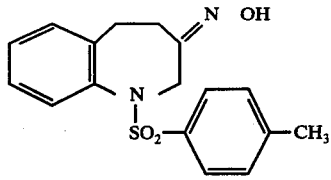

reducing the latter to form a compound of the formula

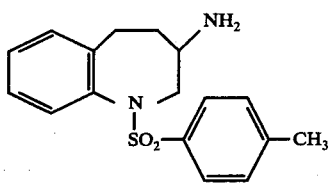

and reacting the latter with sodium in ammonia to obtain a compound of the formula

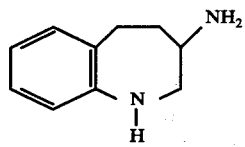

which may be isolated and salified, if desired or the compound of formula Ic may be reacted with formic acid to obtain a compound of the formula

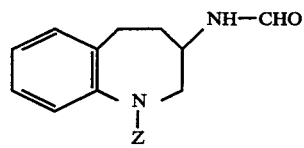

wherein Z has the above definition and reducing the latter to form a compound of the formula

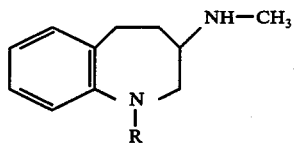

wherein R has the above definition and the latter may be salified, if desired.

In a preferred mode of the process of the invention, the reduction of the compounds of the formulae VI and VIII is effected with lithium aluminum hydride in an anhydrous organic solvent such as tetrahydrofuran and the reaction with sodium in ammonia is preferably effected in an anhydrous organic solvent such as tetrahydrofuran. The reaction of formic acid with a compound of formula Ic is preferably effected with heating.

When it is desired to form a compound of formula V or VIII where Z is hydrogen, only one mole of formic acid is used for each mole of the compound of formula Ia or Ic and when Z is formyl, an excess of the stoichiometric amount of formic acid is used. Preferably 2 to 3 moles of formic acid per mole of compound of formula Ia or Ic are used in the latter case.

Since the compounds of formula I are basic, it is advantageous to form the acid addition salts thereof by reacting substantially stoichiometric amounts of the acid and the free base of formula I.

The novel antidepressive compositions of the invention are comprised of an antidepressively effective amount of at least one compound of formula I and its non-toxic, pharmaceutically acceptable acid addition salts and an inert pharmaceutical carrier. The compositions are also important inhibitors of the collecting of 5HT (serotonine) of synaptosomes and the compositions may be in the form of tablets, dragees, gelules, granules, suppositories and injectable solutions or suspensions prepared in the usual fashion.

Examples of suitable excipients for the compositions are talc, arabic gum, lactose, starch, magnesium stearate, cacao butter, aqueous or non-aqueous vehicles, fatty bodies of animal or vegetable origin, paraffinic derivatives, glycols, preservatives, diverse wetting agents, emulsifiers or dispersants.

The compositions are useful for the treatment of depression, melancholy, manic-depressive psychosis, reactional and exhausted depressions and neurotic depressions.

The novel method of the invention for combatting depression in warm-blooded animals including humans comprises administering to warm-blooded animals an antidepressively effective amount of at least one compound of formula I and its non-toxic, pharmaceutically acceptable acid addition salts. The compounds may be administered orally, rectally or parenterally and the usual useful dose is depending on the compound, the methods of administration and the condition being treated, and for example, it is 0.2 mg to 6 mg/kg by oral rout in human.

The novel intermediate products of the invention have the formulae

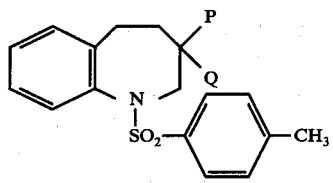

wherein P is —OH and Q is —CN and P is hydrogen when Q is —NH$_2$ and P and Q together form =N—OH;

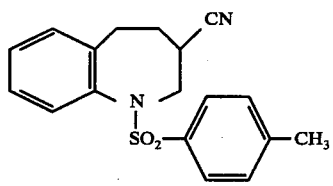

wherein the dotted line is a double bond in the 2,3- or 3,4-position of the ring; and

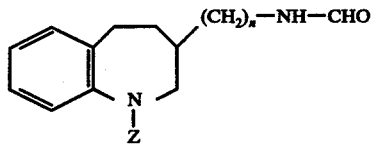

wherein n and Z have the above definitions.

The starting compound of formula II may be prepared by the process described in J. Chem. Soc., Vol. C (1970), p.2192.

In the following examples there are described several preferred embodiments to illustrate the invention. However, it should be understood that the invention is not intended to be limited to the specific embodiments.

EXAMPLE 1

2,3,4,5-tetrahydro-[1H]-1-benzazepine-3-methanamine fumarate

STEP A:

3-hydroxy-1-(4-methylphenylsulfonyl)-1,2,4,5-tetrahydro-[3H]-1-benzazepine-3-carbonitrile 30 ml of water, 40 ml of acetic acid and 20 g of 1,2,4,5-tetrahydro-N-tosyl-[3H]-1-benzazepine-3-one [J. Chem. So., Vol. C (1970), p.2192] were successively added to 300 ml of ethanol and then 20 g of sodium cyanide were added thereto over 2 minutes. The mixture was stirred for 4 hours at room temperature and was then concentrated to 100 ml under reduced pressure. The mixture was extracted with ether and the ether extracts were washed with water, dried over magnesium sulfate and filtered. The filtrate was evaporated to dryness under reduced pressure to obtain 21 g of raw product which was crystallized from a minimum of ether. The mixture was vacuum filtered to obtain 14 g of 3-hydroxy-1-(4-methylphenylsulfonyl)-1,2,4,5-tetrahydro-[3H]-1-benzazepine-3-carbonitrile in the form of colorless crystals melting at 128°C.

Analysis: $C_{18}H_{18}N_2O_3S$; molecular weight = 342.40. Calculated: %C, 63.14; %H, 5.30; %N, 8.18; %S 9.36. Found: C, 63.1; %H, 5.4; %N, 7.9; %S, 9.4.

STEP B:

4,5-dihydro-1-(4-methylphenylsulfonyl)-[1H]-1-benzazepine-3-carbonitrile and 2,5-dihydro-1-(4-methylphenylsulfonyl)-[1H]-1-benzazepine-3-carbonitrile 1 g of the product of Step A was added over 5 minutes at 20° C under a nitrogen atmosphere to a mixture of 0.5 ml of pyridine and 0.5 ml of thionyl chloride and the mixture was stirred for 15 minutes at 100° C and was then cooled to 20° C. The mixture was poured into 5 ml of ice water and the mixture was extracted with methylene chloride. The organic extracts were washed with water, dried over magnesium sulfate and was filtered. The filtrate was evaporated to dryness to obtain 1 g of a brown residue which was chromatographed over silica gel. Elution with benzene yielded 2 fractions. The first fraction was 500 mg of 4,5-dihydro-1-(4-methylphenylsulfonyl)-[1H]-1-benzazepine-3-carbonitrile in the form of a colorless oil with an Rf = 0.1. The oil was crystallized from a minimum of ether and vacuum filtration yielded 400 mg of the said 4,5-dihydro product in the form of colorless crystals melting at 138° C.

Analysis: $C_{18}H_{18}N_2SO_2$; molecular weight = 324.39. Calculated: %C, 66.64; %H, 4.97; %N, 8.64; %S, 9.88. Found: C, 66.4; H, 5.0; N, 8.5; S, 10.2.

The second fraction was 260 mg of 2,5-dihydro-1-(4-methylphenylsulfonyl)-[1H]-1-benzazepine-3-carbonitrile in the form of an oil with an Rf = 0.05. The latter was crystallized from a minimum of ether and vacuum filtration yielded 160 mg of the said 2,5-dihydro product in the form of colorless crystals melting at 148° C.

Analysis: $C_{18}H_{16}N_2SO_2$; molecular weight = 324.39. Calculated: %C, 66.64; %H, 4.97; %N, 8.64; %S, 9.88. Found: C, 66.5; H, 5.0; N, 8.5; S, 9.7.

STEP C:

2,3,4,5-tetrahydro-[1H]-1-benzazepine-3-methanamine fumarate 60 g of sodium were added over 2 hours in small amounts to a refluxing mixture of 15.6 g of the 4,5-dihydro product of Step B and 500 ml of ethanol and at the end thereof, 100 ml of ethanol were added. The mixture was stirred until the sodium dissolved and the solution was evaporated to dryness under reduced pressure. The residue was extracted with a 1-1 ethyl acetate-ether mixture. The extracts were washed with water, dried over magnesium sulfate and was filtered. The filtrate was evaporated to dryness under reduced pressure to obtain 8.5 g of 2,3,4,5-tetrahydro-[1H]-1-benzazepine-3-methananmine in the form of a yellow oil.

8.5 g of the said product were dissolved in 90 ml of ethyl acetate and a solution of 2.8 g of fumaric acid in 60ml of methanol was added thereto dropwise. The mixture was concentrated and was vacuum filtered to obtain 6.2 g of 2,3,4,5-tetrahydro-[1H]-1-benzazepine-3-methanamine fumarate in the form of colorless crystals melting at ≃ 200° C.

Analysis: $C_{11}H_{16}N_2C_4H_4O_4$; molecular weight = 292.33 Calculated: %C, 61.63; %H, 6.90; %N, 9.58. Found: C, 61.5; H, 7.0; N, 9.5.

EXAMPLE 2

N-methyl-2,3,4,5-tetrahydro-[1H]-1-benzazepine-3-methanamine dihydrochloride

STEP A':

N-[(1-formyl-2,3,4,5-tetrahydro-[1H]-benzazepine-3-yl)-methyl]-formamide

A mixture of 2.4 cm³ of formic acid and 2.4 g of 2,3,4,5-tetrahydro-[1H]-1-benzazepine-3methanamine was refluxed for an hour on a bath at 170° C and excess formic acid was then distilled under reduced pressure. The mixture was cooled and extracted with methylene chloride and the organic extracts were washed with aqueous solution saturated with sodium bicarbonate, dried over magnesium sulfate and filtered. The filtrate was evaporated to dryness under reduced pressure to obtain 2.9 g of an oil which was crystallized from 3 ml of ethyl acetate to obtain 1.7 g of N-[(1-formyl-2,3,4,5-tetrahydro-[1H]-1-benzazepine-3-yl)-methyl]-formamide melting at 128° C. For analysis, 200 mg of the product were dissolved in 30 ml of refluxing ethyl acetate and the solution was filtered and evaporated to 3 ml. The mixture was vacuum filtered to obtain 140 mg of the product in the form of colorless crystals melting at 130° C identical to the product of Step A.

Analysis: $C_{13}H_{16}N_2O_2$; molecular weight = 232.27. Calculated: %C, 67.22; %H 6.94; %N, 12.06. Found: C, 67.2; H, 7.0; N, 11.8.

STEP A:
N-[(2,3,4,5-tetrahydro-[1H]-1-benzazepine-3-yl)-methyl]-formamide and N-[(1-formyl-2,3,4,5-tetrahydro-[1H]-1-benzazepine-3yl)-methyl]-formamide 4.8 g of the fumarate salt of Example 1 were dissolved in 100 ml of refluxing water and the mixture was filtered and cooled. The filtrate was made alkaline with a concentrated ammonium solution and was extracted with methylene chloride. The organic extracts were washed with water, dried over magnesium sulfate and filtered. The filtrate was evaporated to dryness under reduced pressure to obtain 2.9 g of 2,3,4,5-tetrahydro-[1H]-1-benzazepine-3-methanamine in the form of a yellow oil which was cooled on an ice bath. 0.62 ml of formic acid were added thereto and the mixture was stirred and heated for 15 minutes on a bath at 150° C. The mixture was cooled to about 20° C and was dissolved in 30 ml of methylene chloride. The mixture was dried and filtered and the filtrate was evaporated to dryness to obtain 3.3 g of a brown oil which was chromatographed over silica gel. Elution with a 9-1 chloroform-methanol mixture yielded two fractions, the first being 700 mg of N-[(1-formyl-2,3,4,5-tetrahydro-[1H]-1-benzazepine-3-yl)-methyl -formamide as a colorless oil with an Rf = 0.45. The latter was crystallized from 0.5 ml of ethyl acetate and was vacuum filtered to obtain 410 mg of the said product in the form of colorless crystals melting at 130° C. The second fraction was 1.3 g of N-[(2,3,4,5-tetrahydro-[1H]-1-benzazepine-3-yl)-methyl]-formamide in the form of a colorless oil with an Rf = 0.4. The latter was crystallized from 2 ml of ether and was vaccum filtered to obtain 1.25 g of the said product in the form of colorless crystals melting at 120° and then 160° C.

Analysis: $C_{12}H_{16}N_2O$; molecular weight = 204.26. Calculated: %C, 70.56; %H 7.90; %N, 13.72. Found: C, 70.7; H, 7.9; N, 13.7.

STEP B:
N-methyl-2,3,4,5-tetrahydro-[1H]-1-benzazepine-3-methanamine and its dihydrochloride 2 g of lithium aluminum hydride were added to 40 ml of anhydrous tetrahydrofuran and then 2 g of the product of Step A were added over 3 minutes. The mixture was refluxed with stirring for 30 minutes and after cooling the mixture tp 10° C, 40 ml of tetrahydrofuran containing 20% of water were added thereto. The mixture was filtered, washed with methylene chloride and evaporated to dryness. The residue was taken up in methylene chloride and the solution was washed with water, dried over magnesium sulfate, filtered and evaporated to dryness under reduced pressure to obtain 1.9 g of N-methyl-2,3,4,5-tetrahydro-[1H]-1-benzazepine-3-methanamine in the form of a colorless oil.

1.9 g of the said oil were dissolved in 10 ml of ethyl acetate and a solution of ethyl acetate saturated with hydrogen chloride was added thereto dropwise until the pH was just acid. The mixture was vacuum filtered to obtain 2.3 g of dihydrochloride of N-methyl-2,3,4,5-[1H]-1-benzazepine-3-methanamide in the form of colorless crystals melting at 170° C.

Analysis: $C_{12}H_{18}N_2.2HCl$; molecular weight = 263.212. Calculated: %C, 54.75; %H, 7.66; %N, 10.64. Found: C, 54.8; H, 8.0; N, 10.6.

EXAMPLE 3
Di-[N,1-dimethyl-2,3,4,5-tetrahydro-[1H]-1-benzazepine-3-methanamine]-fumarate 3.2 g of N-[(1-formyl-2,3,4,5-tetrahydro-[1H]-1-benzazepine-3-yl)-methyl]-formamide were added over 5 minutes to a temperature less than 20° C to a mixture of 3.2 g of lithium aluminum hydride in 60 ml of anhydrous tetrahydrofuran and the mixture was refluxed for an hour and then cooled to 10° C. 20 ml of tetrahydrofuran containing 40% water were added thereto dropwise and the mixture was filtered. The filtrate was washed with methylene chloride and was evaporated to dryness under reduced pressure to obtain 2.5 g of raw product. The latter was taken up in methylene chloride and the solution was washed with water, dried over magnesium sulfate, filtered and evaporated to dryness to obtain 2.5 g of [N, 1-dimethyl-2,3,4,5-tetrahydro-[1H]-1-benzazepine-3-methanamine].

A solution of 2.5 g of the said product in 5 ml of methanol was added to a solution of 710 mg of fumaric acid in 10 ml of methanol and then 50 ml of ethyl acetate were added thereto. The mixture was concentrated until crystallization and was vacuum filtered to obtain 2.8 g of the fumarate salt in the form of colorless crystals melting at 165° C.

Analysis: $(C_{13}H_{20}N_2)_2 \cdot C_4H_4O_4$; molecular weight = 524.68. Calculated: %C, 68.67; %H, 8.45; %N, 10.68. Found: C, 68.4; H, 8.7; N, 10.6.

EXAMPLE 4
di-[2,3,4,5-tetrahydro-[1H]-1-benzazepine-3-amine]-fumarate

STEP A: oxime of 1-(4-methylphenylsulfonyl)-1,2,4,5-tetrahydro-[3H]-1-benzazepine-3-one A mixture of 2.1 g of 1,2,4,5-tetrahydro-N-tosyl-[3H]-1-benzazepine-3-one [J. Chem. Soc., Vol. C (1970), p.2192 ], 1.05 g of molten sodium acetate, 700 mg of hydroxylamine hydrochloride and 35 ml of ethanol was refluxed for an hour and then cooled to room temperature. The mixture was poured into 200 ml of water and was then vacuum filtered. The product was washed with water and dried under reduced pressure to obtain 2.2 g of the oxime of 1-(4-methylphenylsulfonyl)-1,2,4,5-tetrahydro-[3H]-1-benzazepine-3-one melting at 190°–195° C in the form of a mixture of isomers used as is for the next step.

STEP B: di[1-(4-methylphenylsulfonyl)-2,3,4,5-tetrahydro-[1H]-1-benzazepine-3-amine]-fumarate A solution of 36 g of the product of Step A in 600 ml of anhydrous tetrahydrofuran was added dropwise over 15 minutes to a mixture of 36 g of lithium aluminum hydride in 600 ml of anhydrous tetrahydrofuran and the mixture was stirred for 3½ hours at room temperature and was then cooled to 15° C. 250 ml of tetrahydrofuran containing 30% of water were added dropwise to the mixture at less than 20° C and the mixture was filtered. The filtrate was washed with methylene chloride and was distilled to dryness under reduced pressure. The residue was taken up in methylene chloride and the solution was washed with water, dried over magnesium sulfate and evaporated to dryness under reduced pressure to obtain 28 g of 1-(4-methylphenylsulfonyl)-2,3,4,5-tetrahydro-[1H]-1-benzazepine-3-amine in the form of a yellow oil.

The 28 g of said product were dissolved in 100 ml of ethyl acetate and a solution of 5.1 g of fumaric acid in 60 ml of methanol were added thereto. The mixture was concentrated to 100 ml under reduced pressure and was vacuum filtered to obtain 28.5 g of the fumarate salt of the said product in the form of colorless crystals melting at 135° C and then 190° C.

Analysis: $(C_{17}H_{20}N_2O_2S)_2 \cdot C_4H_4O_4$; molecular weight = 748.9. Calculated: %C, 60.94; %H, 5.92; %N, 7.48; %S, 8.56. Found: C, 61.1; H, 6.1; N, 7.4; S, 8.8.

STEP C:
di-[2,3,4,5-tetrahydro-[1H]-1-benzazepine-3-amine]-fumarate 10 g of the product of Step B were added over 5 minutes at −40° C to a mixture of 750 ml of dry ammonia and 100 ml of anhydrous tetrahydrofuran and then small quantities of sodium were added thereto at −50° C until a blue coloration persisted (about 4 g over 90 minutes). The mixture was stirred for 15 minutes and then small quantities of ammonium chloride were added until the color disappeared (about 2 g in 10 minutes). The ammonia was distilled and the mixture was poured into 500 ml of water. The mixture was extracted with methylene chloride and the extracts were washed with water, dried over magnesium sulfate, filtered and evaporated to dryness to obtain 4.3 g of 2,3,4,5-tetrahydro-[1H]-1-benzazepine-3-amine in the form of a yellow oil.

The said product was dissolved in 30 ml of isopropanol and a solution of 1.5 g of formic acid in 20 ml of methanol was added thereto. The mixture was concentrated to 30 ml and was vacuum filtered to obtain 4 g of di-[2,3,4,5-tetrahydro-[1H]-1-benzazepine-3-amine]-fumarate in the form of beige crystals melting at 245° C.

Analysis: $(C_{10}H_{14}N_2)_2 \cdot C_4H_4O_4$; molecular weight = 440.52. Calculated: %C, 65.43; %H, 7.32; %N, 12.72. Found: C, 65.3; H, 7.4; N, 12.4.

EXAMPLE 5
di-[N,1-dimethyl-2,3,4,5-tetrahydro-[1H]-1-benzazepine-3-amine]-fumarate

STEP A':
N-(1-formyl-2,3,4,5-tetrahydro-[1H]-1-benzazepine-3-yl)-formamide

A mixture of 5.5 g of 2,3,4,5-tetrahydro-[1H]-1-benzazepine-3-amine and 5.5 ml of formic acid was refluxed for an hour in a bath of 150° C and the mixture was then distilled to dryness under reduced pressure. The residue was taken up in methylene chloride and the organic extracts were washed with a saturated aqueous sodium bicarbonate solution, dried over magnesium sulfate, filtered and evaporated to dryness under reduced pressure. The residue was crystallized from about 10 ml of ethyl acetate and was vacuum filtered to obtain 6.4 g of N-(1-formyl-2,3,4,5-tetrahydro-[1H]-1-benzazepine-3-yl)-formamide melting at 130° C. For analysis, the 130 mg of the product were dissolved in 5 ml of refluxing isopropanol and the solution was filtered and concentrated to 1 ml. After crystallization, the product was vacuum filtered, washed with isopropanol and dried to obtain 50 mg of the said product in the form of colorless crystals melting at 130° C which is identical to the product of Step A.

Analysis: $C_{12}H_{14}N_2O_2$; molecular weight = 218.25. Calculated: %C, 66.03; %H, 6.47; %N, 12.84. Found: C, 66.0; H, 6.6; N, 12.6.

STEP A:
N-(2,3,4,5-tetrahydro-[1H]-1-benzazepine-3-yl)-formamide and
N-(1-formyl-2,3,4,5-tetrahydro-[1H]-1-benzazepine-3-yl)-formamide A mixture of 600 ng of 2,3,4,5-tetrahydro-[1H]-1-benzazepine-3-amine and 0.14 ml of formic acid was stirred for 30 minutes in a bath at 145°–150° C and after cooling to about 20° C, the mixture was extracted with methylene chloride. The organic extracts were washed with aqueous sodium bicarbonate solution and then with water, dried over magnesium sulfate, filtered and evaporated to dryness under reduced pressure. The 630 mg of raw product in the form of a deep orange oil were chromatographed over silica gel and was eluted with ethyl acetate to obtain 2 fractions. The first fraction was 350 mg of N-(2,3,4,5-tetrahydro-[1H]-1-benzazepine-3-yl)-formamide with a Rf = 0.15. The latter was empasted with a minimum of ether and was vacuum filtered to obtain 300 mg of the said product in the form of colorless crystals melting at 124° C.

Analysis: $C_{11}H_{14}N_2O$; molecular weight = 190.24. Calculated: %C, 69.44; %H, 7.42; %N, 14.73; %O, 8.14. Found: C, 69.1; H, 7.4; N, 14.4; O, 8.7.

The second fraction was 120 mg of N-(1-formyl-2,3,4,5-tetrahydro-[1H]-1-benzazepine-3-yl)-formamide with an Rf = 0.10 which was empasted with a minimum of ethyl acetate to obtain 70 mg of the said product melting at 130° C.

STEP B:
di-[N,1-dimethyl-2,3,4,5-tetrahydro-[1H]-1-benzazepine-3-amine]-fumarate 2.5 g of the 1-formyl compound of Step A were added in 2 to 3 minutes to a mixture of 2.5 g of lithium aluminum hydride in 50 ml of anhydrous tetrahydrofuran and the mixture was refluxed with stirring for 2 hours and was then cooled to 10° C. 25 ml of tetrahydrofuran containing 30% of water was added thereto dropwise and the mixture was filtered. The filtrate was washed with methylene chloride and was evaporated to dryness under reduced pressure to obtain 2.1 g of raw product. The latter was chromatographed over silica gel and was eluted with an 8-1-1 chloroform-methanol-triethyl-amine mixture to obtain a first yield of 1.1 g of N,1-dimethyl-2,3,4,5-tetrahydro-[1H]-1-benzazepine-3-amine in the form of a yellow oil with an Rf = 0.6 and a second yield of 750 mg of N-methyl-2,3,4,5-tetrahydro-[1H]-1-benzazepine-3-amine in the form of a colorless oil with an Rf = 0.25.

The 1.1 g of the first product were dissolved in 30 ml of ethyl acetate and a solution of 0.335 g of formic acid 10 ml of methanol was added thereto. The mixture was concentrated under reduced pressure to 10 ml and was vacuum filtered to obtain 900 mg of di-[N, 1-dimethyl-2,3,4,5-tetrahydro-[1H]-1-benzazepine-3-amine]-fumarate in the form of colorless crystals melting at 145° C.

Analysis: $C_{24}H_{36}N_4 \cdot C_4H_4O_4$; molecular weight = 496.64. Calculated: %C, 67.71; %H, 8.12; %N, 11.28. Found: C, 67.4; H, 8.1; N, 11.0.

EXAMPLE 6 di-[N-methyl-2,3,4,5-tetrahydro-[1H]-1-benzazepine-3-amine] fumarate

A solution of 247 mg of fumaric acid in 10 ml of methanol was added to a solution of 750 mg of N-methyl-2,3,4,5-tetrahydro-[1H]-1-benzazepine-3-amine in 30 ml of ethyl acetate and the mixture was concentrated under reduced pressure to 10 ml and was vacuum filtered to obtain 900 mg of raw product. The latter was dissolved in methanol and the solution was filtered. The filtrate was added to isopropanol and the mixture was concentrated until crystallization occured. The mixture was vacuum filtered to obtain 820 mg of di-[N-methyl-2,3,4,5-tetrahydro-[1H]-1-benzazepine-3-amine] fumarate in the form of colorless crystals melting at 190° C.

Analysis: $(C_{11}H_{16}N_2)_2 \cdot C_4H_4O_4$; molecular weight = 468.58. Calculated: %C, 66.64; %H, 7.74; %N, 11.96. Found: C, 66.7; H, 7.7; N, 11.9.

EXAMPLE 7

Tablets were prepared containing 25 mg of either N-methyl-2,3,4,5-tetrahydro-[1H]-1-benzazepine-3-methanamine dihydrochloride or di-[N,1-dimethyl-2,3,4,5-tetrahydro-[1H]-1-benzazepine-3-methanamine]-fumarate and sufficient excipient of lactose, starch, talc and magnesium stearate to obtain a final weight of 200 mg.

PHARMACOLOGICAL DATA

A. Potentialization of effects of IMAO

The administration to mice of an inhibitor of monoamine oxidase induces a hyperactive motility in the animals which is potentialized by an antidepressive [Carlsson et al, Brain Research, Vol. 12 (1969), p. 456]. A dose of 100 mg/kg of nialamide was administered intraperitoneally 30 minutes before the test product was administered in the same fashion. The values of actimetric countings were totaled every 30 minutes for 6 hours and the potentialization of the effects of nialamide by the test product was expressed by increasing number of + signs for a dose in mg/kg. The results are reported in Table I.

TABLE I

| Product of Example | Dose in mg/kg | Potentialization of nialamide for the dose |
|---|---|---|
| 1 | 1 | ++ |
| 2 | 5 | +++ |
| 3 | 5 | ++ |
| 4 | 20 | ++ |

The results of Table I show that the products potentialize in an important manner the effects of nialamide.

B. Potentialization of effects of 5 HTP

The administration of 5-hydroxytryptophane (5 HTP) to mice pretreated with an antidepressive agent induces in the animals a particular behavoir, namely the appearance of trembling. The test products were administered intraperitoneally in increasing doses one hour before the intraperitoneal injection of 200 mg/kg of 5 HTP and the observed symptoms were noted every 15 minutes for an hour to determine the minimum active dose (MAD) for the test product. The results are reported in Table II.

TABLE II

| Product of Example | MAD in mg/kg |
|---|---|
| 1 | 50 |
| 2 | 10 |
| 3 | 50 |
| 4 | 50 |
| 5 | 50 |
| 6 | 20 |

The results of Table II show that the products potentialize in an important manner the effects of 5 HTP.

C. Potentialization of L-dopa effects

The administration of L-dopa to mice pretreated with iproniazide 18 hours earlier produces a certain number of symptoms: muscular hypertonicity, hyperactivity, agitation, crying, aggressiveness, salivation and exophthalmia. The intensity of these effects is potentialized by administration of an antidepressive agent one hour before the L-dopa administration.

Male mice received intraperitoneally 75 mg/kg of iproniazide 18 hours before the start of the test and the test products in aqueous solution were administered intraperitoneally in increasing doses. The L-dopa was intraperitoneally administered at a dose of 100 mg/kg one hour later and the symptoms observed 15 and 30 minutes after the L-dopa administration were evaluated on a scale of 0 to 3 for each mouse and the values were totaled for each dose. The $ED_{50}$, the dose at which 50% of the L-dopa effects were potentialized, was determined and the results are reported in Table III.

TABLE III

| Product of Example | $ED_{50}$ in mg/kg |
|---|---|
| 1 | 10 |
| 3 | 20 |
| 4 | 50 |

The results of Table III show that the products potentialized in an important manner the effects of L-dopa.

D. Acute toxicity

The $LD_{50}$, dose which killed 50% of mice was determined by intraperitoneal administration of the test compounds and the mortality rate was determined of 48 hours. The results are reported in Table IV.

TABLE IV

| Product of Example | $LD_{50}$ in mg/kg |
|---|---|
| 1 | 300 |
| 2 | 250 |
| 3 | 250 |
| 4 | 300 |
| 5 | 150 |
| 6 | 250 |

E. Biochemical Study

1. Inhibition of uptake of serotonine in vitro

The inhibition of uptake of serotonine (5 HT) was measured with purified synaptosoma prepared by starting from the whole brain of female rats 19–21 days old by the technique of Kannengiesser et al [Biochemical Pharmacology, Vol. 22 (1973), p. 73]. The test products at different concentrations were incubated with the preparation at 37° C for 5 minutes in the presence of $C^{14}$- 5 HT at a concentration of $10^{-7}$ M. The 50% inhibiting concentration (IC 50) of the products was graphically determined as the dose that inhibited by 50% the uptake of $C^{14}$- 5 HT in the synaptosma. The results are reported in Table V.

2. Inhibition of uptake of serotonine in vivo

The test products were administered intraperitoneally to groups of female rats 19 to 21 days old at doses from 5 to 20 mg/kg. After 30 minutes, the brain was removed and the synaptosoma was prepared and was placed in an incubator in the presence of $C^{14}$- 5 HT as indicated previously. The relative power of the products to inhibit the uptake of $C^{14}$- 5 HT is estimated by the ratio of a test effected with animals which did not receive the test products. The activity is expressed in % inhibition with respect to the controls at a dose of 10 mg/kg and the results are reported in Table V.

TABLE V

| Product of Example | Test No. 1 | Test No. 2 |
|---|---|---|
| 2 | $13 \times 10^{-7}$ | 58 |
| 3 | $13 \times 10^{-7}$ | 40 |

The results of Table V show that the compounds possess very interesting serotoninergic properties.

Various modifications of the products and methods of the invention may be made without departing from the spirit or scope thereof and it should be understood that the invention is intended to be limited only as defined in the appended claims.

We claim:

1. A compound selected from the group consisting of benzazepines of the formula

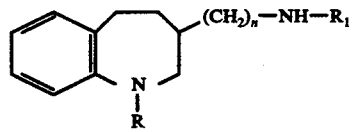

wherein $n$ is 0 or 1 and R and $R_1$ are individually selected from the group consisting of hydrogen and methyl with the proviso that when $R_1$ is methyl, R is also methyl and their non-toxic, pharmaceutically acceptable acid addition salts.

2. A compound of claim 1 wherein $n$ is 1.

3. A compound selected from the group consisting of 2,3,4,5-tetrahydro-[1H]-1-benzazepine-3-methanamine and its non-toxic, pharmaceutically acceptable acid addition salts.

4. A compound selected from the group consisting of N-methyl-2,3,4,5-tetrahydro-[1H]-1-benzazepine-3-methanamine and its non-toxic, pharmaceutically acceptable acid addition salts.

5. A compound selected from the group consisting of N,1-dimethyl-2,3,4,5-tetrahydro-[1H]-1-benzazepine-3-methanamine and its non-toxic, pharmaceutically acceptable acid addition salts.

6. An antidepressive composition comprising an antidepressively effective amount of at least one compound of claim 1 and an inert pharmaceutical carrier.

7. A composition of claim 6 wherein $n$ is 0.

8. A composition of claim 6 wherein the compound is selected from the group consisting of 2,3,4,5-tetrahydro-[1H]-1-benzazepine-3-methanamine; N-methyl-2,3,4,5-tetrahydro-[1H]-1-benzazepine-3-methanamine; N,1-dimethyl-2,3,4,5-tetrahydro-[1H]-1-benzazepine-3-methanamine and their non-toxic, pharmaceutically acceptable acid addition salt.

9. A method of relieving depression in warm-blooded animals comprising administering to warm-blooded animals an antidepressant amount of at least one compound of claim 1.

10. The method of claim 9 wherein $n$ is 0.

11. The method of claim 9 wherein the compound is selected from the group consisting of 2,3,4,5-tetrahydro-[1H]-1-benzazepine-3-methanamine; N-methyl-2,3,4,5-tetrahydro-[1H]-1-benzazepine-3-methanamine; N,1-dimethyl-2,3,4,5-tetrahydro-[1H]-1-benzazepine-3-methanamine and their non-toxic, pharamaceutically acceptable acid addition salt.

* * * * *